United States Patent [19]

Hildebrand et al.

[11] 4,396,287
[45] Aug. 2, 1983

[54] SAMPLE MANIPULATION SYSTEM FOR SPECTROMETERS

[75] Inventors: Karl J. Hildebrand, Tyngsboro; John Leeman, Andover, both of Mass.

[73] Assignee: Leeman Labs Inc., Tewksbury, Mass.

[21] Appl. No.: 260,334

[22] Filed: May 4, 1981

[51] Int. Cl.³ ............................................ G01N 21/74
[52] U.S. Cl. ..................................... 356/244; 356/312
[58] Field of Search .................. 356/312, 244; 422/36, 422/38, 78, 80; 73/863, 863.11; 219/271, 272

[56] References Cited

U.S. PATENT DOCUMENTS

| 3,832,060 | 8/1974 | Dahlquist | 356/36 |
| 4,008,963 | 2/1977 | Hufer et al. | 356/312 |
| 4,111,553 | 9/1978 | Garnys | 356/244 |

Primary Examiner—F. L. Evans
Assistant Examiner—L. A. Dietert
Attorney, Agent, or Firm—John M. Brandt

[57] ABSTRACT

A sample manipulation system for spectrometers is disclosed in which an electrically conductive filament is arranged to receive and hold a liquid containing sample. Various levels of electrical power are employed to heat the filament for such purposes as increasing the affinity of the filament for the liquid, evaporating the liquid after deposition, ashing the remaining sample, and exciting the sample. Separate contact points are provided for each power level as well as means to successively connect at least one end of the filament to each contact point.

9 Claims, 7 Drawing Figures

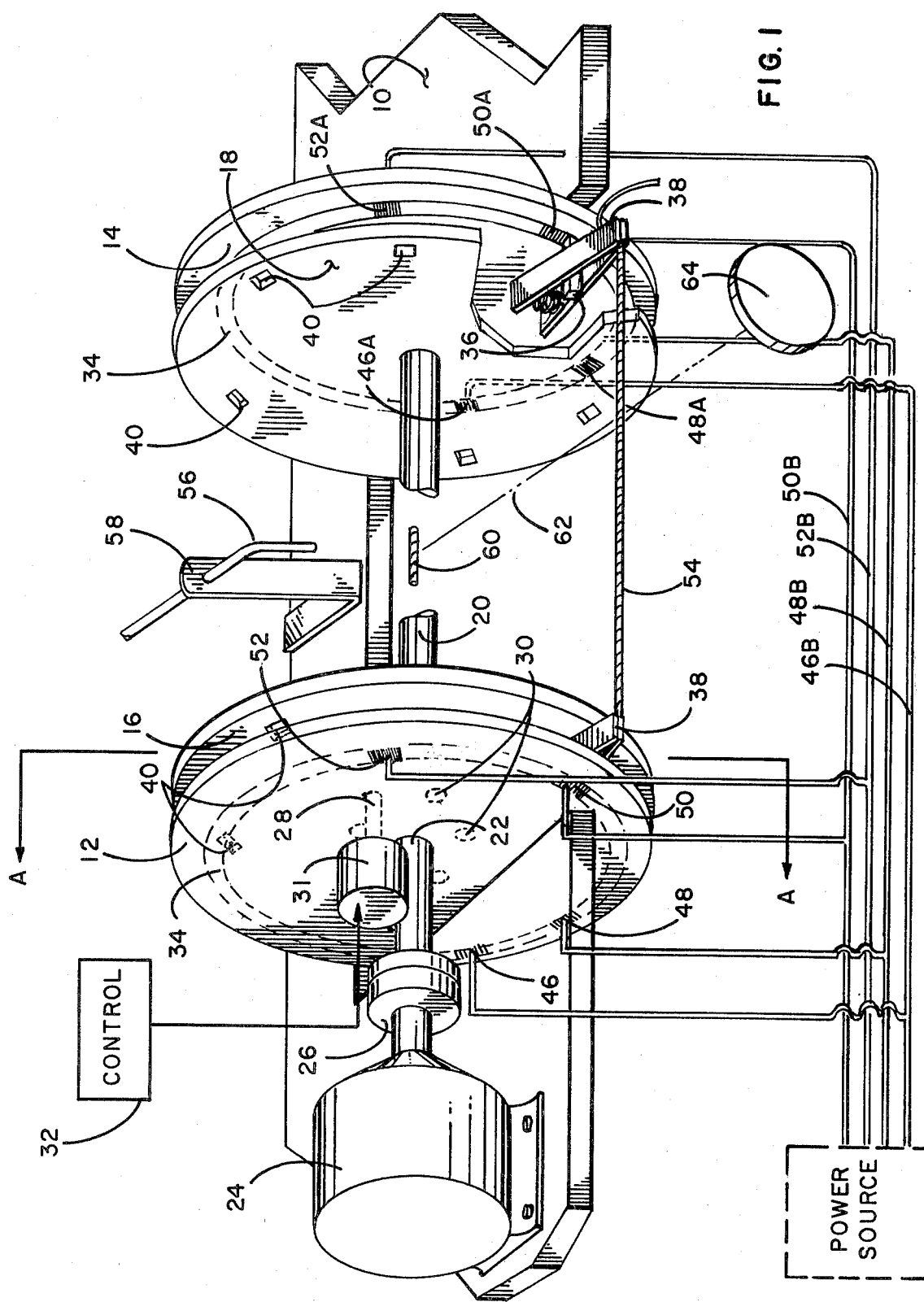

SAMPLE MANIPULATION SYSTEM FOR SPECTROMETERS

BACKGROUND OF THE INVENTION

1. Field of the Invention

The invention resides in the field of analytical spectrometers and more particularly relates to devices for preparing and manipulating samples for presentation to the optical component of the spectrometer.

2. Description of the Prior Art

Spectrometers and associated devices for the introduction and excitation of samples to be analyzed are well known in the prior art. One of the greatest areas of difficulty encountered in these instruments is the introduction of a representative sample into an excitation device such as a flame. In order to assure homogeniety of the sample to be analyzed, it is common practice to dissolve the sample, if not already in solution, and present the sample to the instrument in liquid form.

This practice, while dealing effectively with some of the problems of sample integrity, poses other problems in the excitation and analysis system. For example, the sample is usually nebulized and introduced into the excitation device as a mist of fine droplets. Pneumatic nebulizers are generally used and their efficiency is low, commonly 20 to 25%.

Further, the excitation process in prior art instruments includes desolvation, molecular dissociation, and atomic excitation all at one situs. As a result, a large fraction of the energy supplied to the excitation device is used in desolvation.

Additionally, the solvent is often a source of background interference in the measurement and the materials to be analyzed are present in a very dilute form, typically 1% sample in the final solution.

In spectrometers of more recent manufacture, non-flame excitation devices which operate through the dissipation of electrical energy have increasingly supplanted the use of traditional flame atomizers. These take the form of furnaces, rods, and filaments to which electrical power is applied to achieve the desired results.

In response to the problems described above, instruments have been devised which utilize graphite braid to support and supply energy to samples of minute quantity. These filaments have been heated to required temperatures by variable power sources employing electronic switching and feedback control to modulate the power supplied to the braid.

In contrast, the invention disclosed herein presents a system which connects a filament successively to a plurality of contact points, each supplying a level of power to accomplish a particular purpose such as desolvation, ashing, and excitation. By utilizing separate contacts, either the filament or the contacts may be moved to effect a change in power allowing a number of filaments to undergo heating simultaneously. Thus one filament and sample may successively be carried through preparatory and excitation steps while others are subjected to similar treatment in a progressive manner. In this way, an automatic cycle may be established to allow the analysis of samples on a periodic and regular basis yielding a continuous determination of the content of the material from which the sample is drawn.

This feature is particularly useful in the analysis of waste effluents, gases and liquids, which are the products of continuous industrial operations.

Other features and advantages of the invention will become more clear from the summary and description of the preferred embodiment which follow.

SUMMARY OF THE INVENTION

The invention may be summarized as a sample manipulation system for spectrometers comprising an electrically conductive filament, preferably, although not necessarily, a graphite filament, which will receive and hold a sample dissolved or suspended in a liquid. Electrical power is supplied to the filament resulting in the heating of the filament by resistance. Various levels of power are applied by connecting the filament to separate contact points each having a separate level of power, to produce successive levels of heat. The filament may remain stationary and the contact points moved sequentially into position and contact, or, preferably, at least one end of the filament moved from contact point to contact point. The contacts may have a common ground or may be arranged in sets depending upon the geometrical configuration of the instrument.

The apparatus comprising the invention is more particularly described in the description of the preferred embodiment and drawing below.

DESCRIPTION OF THE DRAWINGS

FIG. 1 is a perspective view of the preferred embodiment of the invention;

DESCRIPTION OF THE PREFERRED EMBODIMENT

Figure 3:
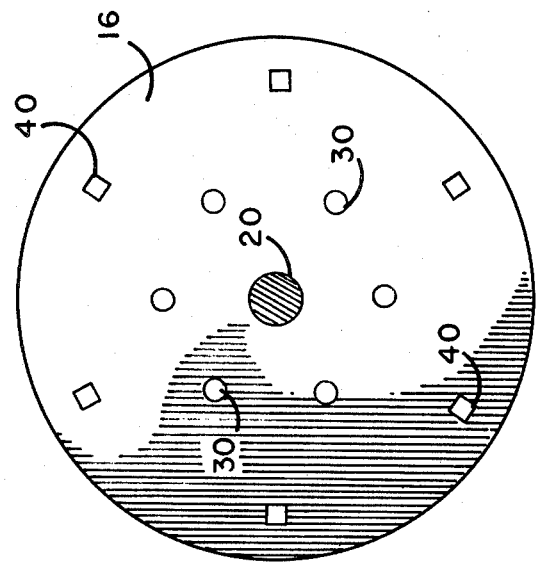
FIG. 3 is an end view of another element of FIG. 1.

Referring to FIG. 1, there is shown a perspective view of the preferred embodiment of the invention in which base 10 supports fixed discs 12 and 14, which in turn support axle 20 having rotatable discs 16 and 18 joined thereto. Axle 20 extends through discs 12 and 14 and is arranged to rotate in the bearing surface created by the passages shown, for example, at 22 on disc 12. Motor 24, mounted on base 10 and connected to axle 20 through slip clutch 26, drives the entire rotatable assembly consisting of discs 16 and 18 and axle 20. Pin 28 slideably mounted in disc 12 is arranged to engage holes 30 in disc 16. Solenoid 31 actuated by control 32 operates to insert pin 28 into and withdraw pin 28 from holes 30 to allow the rotatable assembly to revolve and advance by steps.

Tracks 34 lie about the inner peripheries of discs 12 and 14 and are arranged to receive mounting lugs 36 of clamps 38. Holes 40 are positioned in spaced apart relation in discs 16 and 18 and are also arranged to receive mounting lugs 36 of clamps 38.

Electrical contact points consisting for example of thin metallic strips are placed in the outer wall of each track 34. The points comprise a plurality of sets 46–46A, 48–48A, 50–50A, and 52–52A, each of which is connected to a separate electrical power line 46B, 48B, 50B, and 52B. Each line supplies a separate increasing level of power appropriate for the amount of heat required to perform a particular function in the manipulation cycle.

In operation, an electrically conducting filament, such as a length of graphite braid 54 available from Union Carbide Co., Parma, Ohio, is tautly stretched between an opposing pair of clamps. Upon rotation into position in which the clamp mounting lugs 36 come in contact with points 46 and 46A, an amount of power is supplied to warm the braid to increase its affinity for a liquid containing sample which is dispensed onto the braid from pipe 56 mounted on plate 58.

The braid is then rotated by activation of solenoid 31 to points 48 and 48A where a greater amount of power is available to cause desolvation or drying of the sample. Further heating at points 50 and 50A will optionally serve to ash the sample, i.e. remove organic constituents by combustion, if required. Final rotation to points 52 and 52A will bring the braid to a level of power which will produce excitation of the sample at region 60 sufficient for spectrometric analysis. The optical input aperture of a spectrometer is aligned with region 60 as indicated by optical axis 62 and lens 64.

Figure 2:
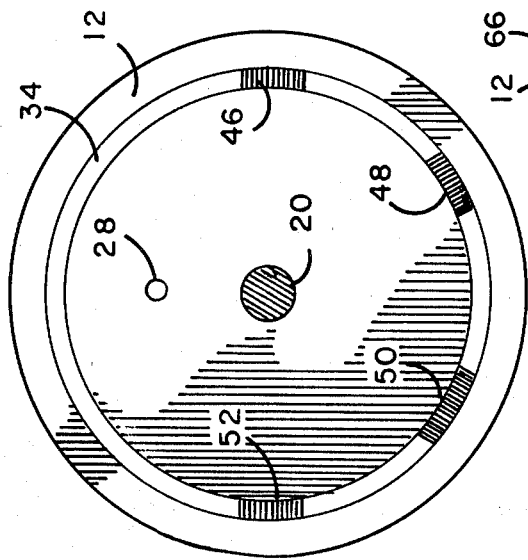
FIG. 2 is an end view of one element of FIG. 1.
Figure 4:
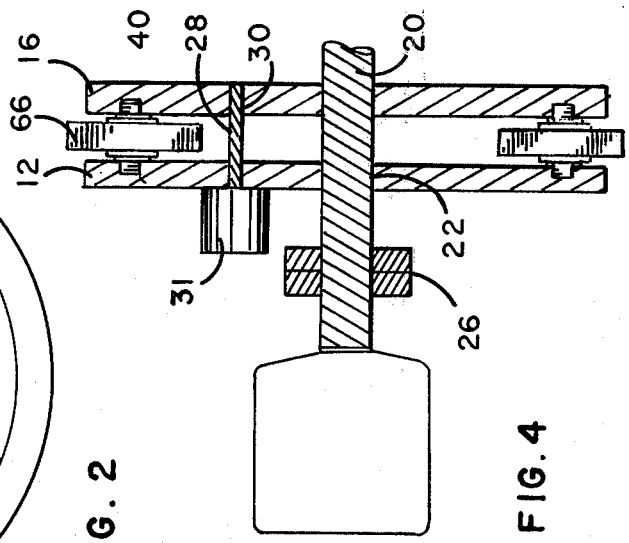
FIG. 4 is a cross-sectional view of FIG. 1 along line A—A.

FIGS. 2, 3, and 4 serve to clarify the mechanical configuration of the apparatus of FIG. 1. Like numerals refer to like parts.

Figure 6:
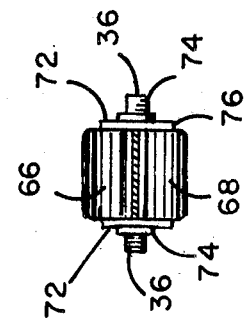
FIG. 6 is a front view of the apparatus of FIG. 5.
Figure 5:
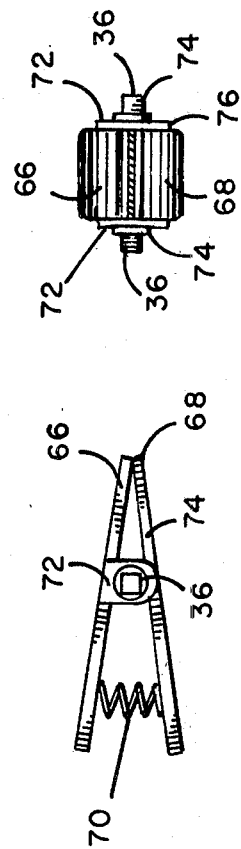
FIG. 5 is a side view of a portion of the apparatus of FIG. 1.

FIGS. 5 and 6 illustrate in detail a clamp suitable for use in the above described apparatus. Jaws 66 and 68 are biased by coil spring 70 and are held togethr by arms 72 attached to jaw 66. Arms 72 rotate about posts 74 secured to jaw 68. Lugs 36 extend from posts 74 and fit track 34 and holes 40 in discs 12 and 16 as previously discussed. Serrations 76 serve to firmly hold the filament in place.

As will be obvious from the above disclosure, there are various alternatives to the preferred embodiment which may be employed within the scope of the invention. For example, one fixed disc may have a single contact which serves as a common ground. The filaments might remain fixed and the contact points brought into sequential contact. Further, the filament might be moved linearly or one end might remain fixed and the other moved from contact to contact.

Figure 7:
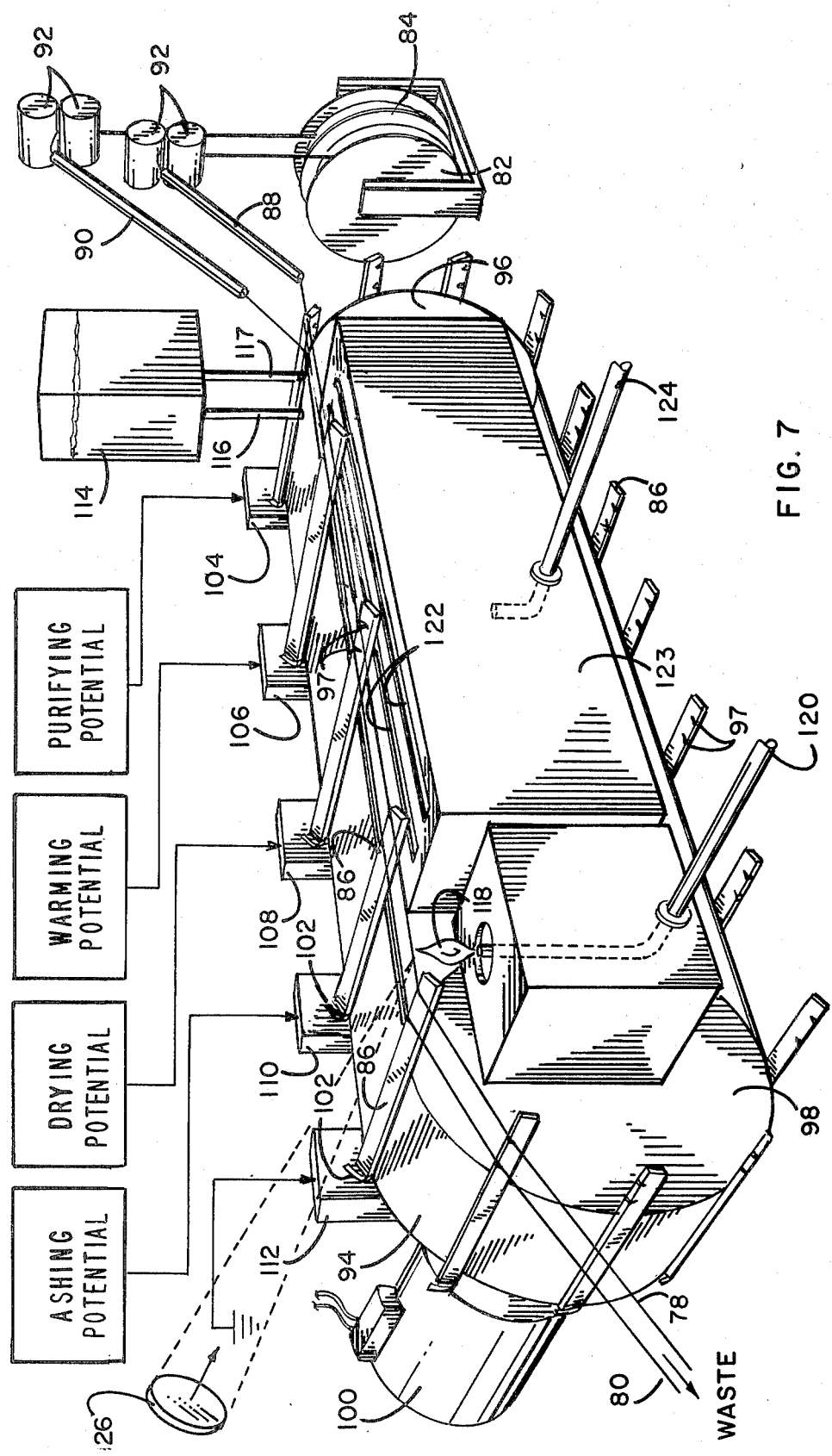
FIG. 7 is a perspective partially schematic view of an additional embodiment of the invention.

Referring next to FIG. 7, an alternative embodiment is illustrated in which electrically conducting graphite filaments 78 and 80 wound on spools 82 and 84 are supplied to transport clamps 86 through leads 88 and 90. Tensioning rollers 92 restrained by spring loading means not shown provide sufficient resistance to render the braid taut. The clamps consist of electrically conducting bars into which are cut V grooves 97 which function to bind the braid at their apex. The clamps are attached to and transported by insulating belt 94 stretched between rotatable roller 96 and rotatable roller 98 driven by electrical motor 100. The bars are inclined at a slight angle to facilitate the binding action.

Each clamp bar has an electrical contact 102 positioned at the end opposite the V grooves to engage electrical power supply contact bars 104, 106, 108, 110, and 112. The clamp bar contact may be a wiper spring as shown or a roller or any other convenient device. Each bar is supplied with a separate level of electrical power or potential. Bar 104, for example, is supplied with sufficient power for purifying the braid, bar 106 to create dispensation affinity, bar 108 for desolvation, and bar 110 for ashing. Bar 112 serves as a ground.

Liquid sample is dispensed from reservoir 114 through pipes 116 and 117 on to the braid. A plasma excitation device employed to excite the sample on the braid to energy levels sufficient for spectrometric analysis is shown at 118. A jet of argon surrounds the plasma and is delivered to the excitation region through pipe 120.

To prevent contamination, the braid is constantly subjected to an argon bath supplied through exit ports 122 in distribution chamber 123 and supplied from pipe 124. Imaging of the excitation region is accomplished by any well-known optical system represented in part by focusing lens 126.

What is claimed is:

1. A sample manipulation system for a spectrometer comprising in combination:
   a. at least one length of electrically conductive filament;
   b. means for supporting said filament;
   c. means for depositing a liquid containing sample over a portion of said filament; and
   d. an electrical power source for heating said filament comprising:
      i. a plurality of separate contact points;
      ii. means for applying variable levels of electrical power to each of said separate points; and
      iii. means for sequentially connecting said filament to said separate points.

2. The apparatus of claim 1 wherein said separate contact points are arranged in sets and said filament is transported sequentially between said sets.

3. The apparatus of claim 1 wherein said means for supporting said filament comprises a pair of clamps.

4. The apparatus of claim 1 wherein said filament is comprised of graphite braid.

5. The apparatus of claim 2 wherein said sets are positioned in curved relationship.

6. A sample manipulation system for a spectrometer comprising in combination:
   a. a length of electrically conducting filament;
   b. means for depositing a liquid containing sample over a portion of said filament;
   c. a plurality of clamps in equidistant spaced apart relationship, said clamps comprising an electrically conducting bar having a V shaped groove in one edge thereof for engaging and securing said filament in the apex of said V;
   d. clamp transport means connected to said clamps for transporting said clamps in equidistant, spaced apart relationship along a selected path of travel, whereby said filament is sequentially advanced along said path;
   e. a plurality of separate electrical contact points positioned along said path positioned to contact said clamps; and
   f. means for applying variable levels of electrical power to each of said separate contact points whereby successive levels of power are applied to successive segments of said filament as said filament is transported by said clamps along said path.

7. The apparatus of claim 6 wherein said clamp transport means comprises:
   a. a belt comprised of an electrically insulating material;
   b. a pair of spaced apart rotatable drums arranged to support said belt; and
   c. electrical motor means arranged to rotate at least one of said drives.

8. The apparatus of claim 6 additionally including;
   a. a second length of electrically conducting filament arranged to be engaged by said clamps in parallel to said first filament; and
   b. means for depositing a liquid containing sample over a portion of said second filament.

9. The apparatus of claim 8 wherein said filaments are comprised of graphite braid.

* * * * *